United States Patent [19]

Halle et al.

[11] 4,285,877

[45] Aug. 25, 1981

[54] DI(2-METHYL-2-PHENYL PROPYL) PEROXY DICARBONATE AND OTHER NOVEL (2-ALKYL-2-PHENYL) SUBSTITUTED PEROXY DICARBONATES

[75] Inventors: Reidar Halle, Novato; David Peterson, Hercules, both of Calif.; Michael A. Fisch, Wayne; Koei-Liang Liauw, Wyckoff, both of N.J.

[73] Assignee: Argus Chemical Corporation, Brooklyn, N.Y.

[21] Appl. No.: 112,872

[22] Filed: Jan. 17, 1980

[51] Int. Cl.$^3$ ............................................. C07C 179/14
[52] U.S. Cl. .............................. 260/453 RZ; 260/463
[58] Field of Search .......................... 260/453 RZ, 463

[56] References Cited

U.S. PATENT DOCUMENTS 3,528,956  9/1970  Gerritsen et al. ................ 526/344.2

*Primary Examiner*—Henry R. Jiles
*Assistant Examiner*—Robert C. Whittenbaugh
*Attorney, Agent, or Firm*—Townsend and Townsend

[57] ABSTRACT

Novel peroxydicarbonates are provided in which the alkyl carbonate moiety is 2-alkyl-2-phenyl substituted. The compounds are useful as polymerization initiators of ethylenically unsaturated monomers, such a vinyl chloride, and as catalysts of unsaturated polyester resins. The subject peroxydicarbonates are characterized in that they are solid at room temperature, have ambient temperature stability in spite of a low 10 hour half-life temperature, and can normally be transported and stored without refrigeration.

9 Claims, No Drawings

DI(2-METHYL-2-PHENYL PROPYL) PEROXY DICARBONATE AND OTHER NOVEL (2-ALKYL-2-PHENYL) SUBSTITUTED PEROXY DICARBONATES

BACKGROUND OF THE INVENTION

1. Field of the Invention

This invention relates to organic peroxide polymerization initiators and to their use in the polymerization of monomers and in the curing of unsaturated polyesters. In particular, it relates to peroxydicarbonates in which each carbonate moiety is di-substituted at its β carbon atom with an alkyl group and a phenyl group.

2. Brief Description of the Prior Art

U.S. Pat. Nos. 3,499,919 and 3,528,956 disclose dicyclohexylperoxydicarbonates substituted at the 4 position by alkyl, cyclohexyl or cyclohexylalkyl and their use as polymerization catalysts.

U.S. Pat. No. 3,720,700 discloses the chemical compound di-cetylperoxydicarbonate, its method of production and its use as an initiator in the polymerization of unsaturated compounds such as vinyl chloride.

U.S. Pat. No. 4,137,252 discloses dicyclododecyl peroxydicarbonate as an improved initiator which is stable and can be stored at room temperature.

U.S. Pat. No. 3,855,351 teaches the use of di-(2-phenoxyethyl) peroxydicarbonate as a polymerization initiator and as a catalyst for curing polyester resins.

SUMMARY OF THE INVENTION

The present invention comprises peroxydicarbonates which are alkyl carbonates having from 3 to 7 carbon atoms in the alkyl chain and joined by a peroxy bond. The two alkyl moieties are each disubstituted at the β carbon with an alkyl group of from 1–4 carbon atoms and a substituted or unsubstituted phenyl group.

The novel compounds of the instant invention have utility as polymerization initiators for monomers having ethylenic unsaturation, such as vinyl chloride, ethylene, styrene and methyl methyacrylate. Similarly, the compounds are useful as catalysts for curing unsaturated polyester resins.

The peroxydicarbonates of the instant invention are particularly advantageous in that they are solid at room temperature. Their solid state imparts ambient temperature stability in spite of their low 10-hour half-life temperature. As a result, the instant peroxydicarbonates can normally be transported and stored without refrigeration. While a low 10-hour half-life temperature is typical of peroxydicarbonates, many known peroxydicarbonates are unstable at room temperature. Some, such as diisopropyl, di-n-butyl and dicyclohexyl peroxydicarbonates decompose explosively at slightly elevated temperatures.

DESCRIPTION OF THE SPECIFIC EMBODIMENT

The peroxydicarbonates of the present invention are those having the formula:

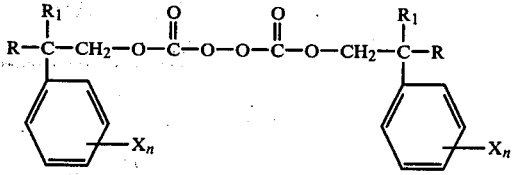

wherein R and $R_1$ are each lower alkyl of from 1 to 4 carbon atoms; n is 0 to 3; and X is selected from the group of lower alkyl of from 1 to 4 carbon atoms, halogen, and lower alkoxy of from 1 to 4 carbon atoms.

In the preferred embodiment the compounds are di(2-alkyl-2-phenyl propyl) peroxy dicarbonates wherein R is methyl and n is zero.

The compounds of the present invention may be prepared by reacting a corresponding haloformate, typically a chloroformate, with hydrogen peroxide in the presence of a base in accordance with the following equation:

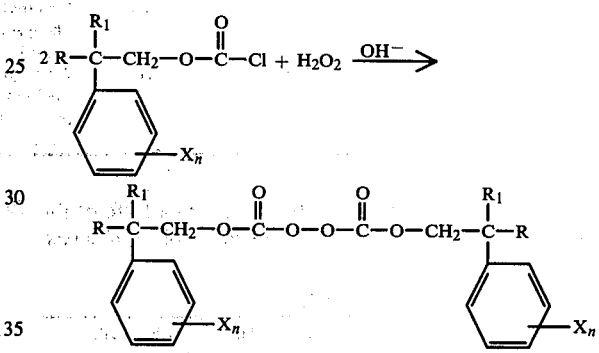

wherein R, $R_1$, X and n are as described above.

The haloformates are prepared by conventional methods.

The following examples are illustrative of the synthesis of the peroxydicarbonates of the present invention and of their utility as polymerization initators. As will be obvious and understood, other compounds within the scope of this invention may be formed by selecting appropriate reactants and quantities, and thus the examples provided should not be construed as limiting the scope of the invention.

EXAMPLE I

Typical Experimental Procedure—Preparation of Di(2-methyl-2-phenyl propyl) peroxydicarbonate (2M2PPPD)

To 10.00 gm (0.043 mole) of 90.6% 2-methyl-2-phenyl propyl chloroformate and 5 ml of isopropanol cooled in an ice bath was added 1.92 gm (0.028 mole) of 50% $H_2O_2$ and 5 ml of isopropanol. After 10 minutes, 0.1 gm of methyl tricaprylyl ammonium chloride was added. Then 3.80 gm (0.0475 mole) of 50% NaOH and 1.0 gm of $H_2O$ were added at 5° C. over 30 minutes. The mixture was stirred at 20° C. for 1 hour and then added to 700 ml of $H_2O$. The solid was washed with methanol and dried under vacuum to give 6.28 gm of 2M2PPPD. Product active oxygen analysis: theory 4.14; found 3.76, 90.8% pure; 68.6% yield. The product had a m.p. of 59°–60° C.

The following Table A lists other peroxydicarbonates of the instant invention which can be prepared according to the Typical Experimental Procedure of Example I using the starting haloformates listed:

TABLE A

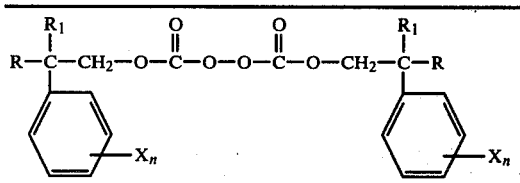

| n | X | R | $R_1$ | Peroxydicarbonate of The Present Invention Starting Haloformate |
|---|---|---|---|---|
| 0 | — | $CH_3$ | $C_2H_5$ | 2-methyl-2-phenyl-propyl chloroformate |
| 0 | — | $C_2H_5$ | $C_2H_5$ | 2-ethyl-2-phenyl-butyl chloroformate |
| 1 | $OCH_3$ | $CH_3$ | $CH_3$ | 2-methyl-2-(methoxy phenyl)-propyl chloroformate |
| 1 | $CH_3$ | $C_3H_7$ | $CH_3$ | 2-methyl-2-(methyl phenyl)-pentyl chloroformate |
| 1 | $C_4H_9$ | $CH_3$ | $C_4H_9$ | 2-methyl-2-(butyl phenyl) hexyl chloro-formate |
| 2 | Cl | $CH_3$ | $CH_3$ | 2-methyl-2-(dichlorophenyl)-propyl chloroformate |

Table I demonstrates that the 10 hour half-life of the compounds of the instant invention are typical of peroxydicarbonates.

TABLE I
THERMAL DECOMPOSITION (HALF-LIFE) FOR Di(2-Methyl-2-Phenyl Propyl) Peroxydicarbonate (Half-Life Data In Benzene)

| Temp, °C. | Half-Life, Hrs. |
|---|---|
| 35 | 17.9 |
| 40 | 8.55 |
| 50 | 1.9 |
| 55 | 0.9 |

10 Hr. Half-Life Temp. = 39° C.

Table II illustrates the storage stability of the instant peroxydicarbonates. At 30° C. for 1 to 4 weeks the compounds still have good storage stability and even at 40° C. they have fair storage stability, particularly for up to 2 weeks.

TABLE II
STORAGE STABILITY OF DI(2-METHYL-2-PHENYL PROPYL) PEROXYDICARBONATE At 30° C. and 40° C.

| | 30° C. | | 40° C. | |
|---|---|---|---|---|
| Days Elapsed | A.O.[1] | % Purity | A.O.[1] | % Purity |
| 0 | 4.05 | 97.8 | 4.05 | 97.8 |
| 7 | 4.03 | 97.4 | 3.95 | 95.4 |
| 14 | 4.05 | 97.8 | 3.85 | 93.1 |
| 28 | 3.95 | 95.4 | 3.30 | 79.8 |

[1] Active Oxygen

As indicated earlier, the instant peroxydicarbonates are useful for initiation of monomers having polymerizable ethylenic or vinyl unsaturation, such as ethylene, styrene, methyl methacrylate and vinyl chloride. The compounds of the present invention are also useful as catalysts in the curing of unsaturated polyester resins.

Tables III and IV demonstrate utility as an initiator of vinyl chloride. The results show the peroxydicarbonates of the instant invention to be efficient initiators in the temperature range of 50°–60° C.

The suspension polymerization were performed in pop bottles using uninhibited monomer. Duplicate bottles were analyzed at each polymerization time interval Bottles were frozen before venting-off excess monomer. The following Table B lists some general information about the polymerization procedure used:

TABLE B

| POLYMERIZATION TEMP., °C. | BOTTLE SIZE, fl. oz. | MIXING SPEED RPM | $H_2O$/VCM Ratio | AMT. SUSPENSION Agent/100g VCM |
|---|---|---|---|---|
| 40 and 50 | 6.5 | 25 | 1.88 | 0.23g Dow Methocel 65 HG, 50 cps |
| 55 and 60 | 12.0 | 42 | 2.50 | 0.35g Dow Methocel 90 HG, 100 cps |

TABLE III
VINYL CHLORIDE POLYMERIZATION With Di(2-Methyl-2-Phenyl Propyl) Peroxydicarbonate

| Temperature °C. | % WT | Moles ($\times 10^{-4}$)/100g VCM | % Conversion |
|---|---|---|---|
| 40 | | | 7 Hours |
| | 0.075 | 1.94 | 28.2 |
| | 0.09 | 2.33 | 31.1 |
| | 0.10 | 2.59 | 41.1 |
| 50 | | | 6 Hours |
| | 0.03 | 0.78 | 30.4 |
| | 0.05 | 1.29 | 46.0 |
| | 0.0627 | 1.62 | 55.1 |
| | 0.075 | 1.94 | 65.0 |
| 55 | | | 5.5 Hours |
| | 0.03 | 0.78 | 42.3 |
| | 0.04 | 1.04 | 51.9 |
| | 0.05 | 1.29 | 65.9[1] |
| | 0.06 | 1.55 | 72.8 |
| | 0.07 | 1.81 | 80.7 |
| 60 | | | 5 Hours |
| | 0.02 | 0.52 | 34.8 |
| | 0.03 | 0.78 | 49.4 |

TABLE III-continued

VINYL CHLORIDE POLYMERIZATION
With Di(2-Methyl-2-Phenyl Propyl) Peroxydicarbonate

| Temperature °C. | % WT | Moles ($\times 10^{-4}$)/ 100g VCM | % Conversion |
|---|---|---|---|
| | 0.04 | 1.04 | 57.9 |
| | 0.05 | 1.29 | 73.2 |

[1]One bottle value

TABLE IV

VINYL CHLORIDE POLYMERIZATION
With Di(2-Methyl-2-Phenyl Propyl) Peroxydicarbonate

| Temperature °C. | % WT | Moles ($\times 10^{-4}$)/ 100g of VCM | % CONVERSION | | | |
|---|---|---|---|---|---|---|
| 50 | 0.10 | 2.59 | HRS | 1 | 2 | 4 6 |
| | | | | 8.8 | 20.9 | 48.8 75.5 |
| 55 | 0.07 | 1.81 | HRS | 1.5 | 3.5 | 5.5 |
| | | | | 21.5 | 62.8 | 79.7 |
| 60 | 0.07 | 1.81 | HRS | 1.5 | 3.5 | 5.0 |
| | | | | 33.6 | 73.8 | 85.7 |

Aside from the selection of the peroxydicarbonates having the structure discussed above, the practice of the present method of polymerizations involving a monomer mass containing one or more monomers, such as ethylene, styrene, methyl methacrylate and vinyl chloride, is consistent with prior art procedures for initiating the polymerization of such monomers. Thus, the present peroxydicarbonates are added in effective amounts, generally comparable to amounts of those initiators previously used, and usually within the range of about 0.005% to 3% by weight of the monomer content and more commonly about 0.01–0.5% by weight of the monomer content. For practical purposes the minimum amount of the peroxydicarbonates is added which will effectively initiate the polymerization of the monomer mass within the desired period of time. The usual conditions of temperature, pressure, solvents, and the like used in the polymerization of these monomers may be employed. In addition, it is contemplated that co-catalysts may be included to initiate the polymerization.

Table V shows results typical of the performance of peroxydicarbonates of the present invention for efficient curing of polyester resins.

TABLE V

HOT BLOCK GEL TESTS WITH POLYESTER RESIN
Using Di(2-Methyl-2-Phenyl Propyl) Peroxydicarbonate[1]

Resin: USS Chemical MR —941 (Isophthalic)
Block Temp.: 180° F. (82° C.)
Concentrations of Peroxide Adjusted to 100% Purity Basis

| TEST | % WT USED | GEL TIME, Min. | EXOTHERM TIME, Min. | PEAK TEMP. °F. (°C.) |
|---|---|---|---|---|
| 1 | 0.48 | 3.08 | 4.82 | 221 (105) |
| 2[2] | 1.0 | 2.83 | 3.70 | 239 (115) |

[1]5cc of a 50g mixture charged to Hot Block
[2]Average values of four determinations Aside from the employment of the novel compounds of the present invention, the practice of the instant method in curing of polyester resins is consistent with known procedures whereby the resin is heated at a curing temperature in the presence of a curing catalyst.

The unsaturated polyester resins cured by the present process comprise a mixture of a linear or only slightly branched polyester resin and a peroxide cross-linkable monomeric compound. The linear or slightly branched polyester resin is typically prepared as a condensation or reaction product of an unsaturated polybasic and a polyhydric compound; for example, the condensation product of an unsaturated dibasic acid of alpha-beta ethylenic unsaturation and a di or trihydric compound, such as a glycol. Often a saturated polybasic acid or anhydride, such as a dibasic acid, is employed with the unsaturated acid or anhydride to modify the reactivity of the unsaturated resin.

Examples of typical polyhydric alcohols include, but are not limited to: ethylene glycol; 1,2-propane diol; 1,3-propane diol; diethylene glycol; dipropylene glycol; triethylene glycol; tripropylene glycol; 1,2-butane diol; 1,3-butane diol; 1,4-butane diol; neopentyl glycol; 2,2,5-trimethylpentane diol; cyclohexanedimethanol; dibromoneopentyl glycol; dibromobutane diol; trimethylolpropane; pentaerythritol; trimethylpentane diol; dipropoxy adducts of bis phenol A; and dipropoxy adducts of hydrogenated bis phenol A.

Examples of saturated polybasic acids include, but are not limited to: isophthalic acid; orthophthalic acid; terephthalic acid; tetrabromophthalic acid; tetrachlorophthalic acid; tetrahydrophthalic acid; adipic acid; succinic acid; azelaic acid; glutaric acid; nadic acid and the various anhydrides obtained therefrom.

Examples of unsaturated polybasic acids include, but are not limited to: maleic acid; fumaric acid; itaconic acid; citraconic acid and anhydrides obtained therefrom.

Examples of peroxide curable cross-linking monomers employed with the linear polyesters include, but are not limited to: styrene, vinyl toluene; acrylates and methacrylates, such as methylmethacrylate; alphamethyl styrene; chloro styrene; and diallyl phthalate. The liquid unsaturated polyester resins also typically contain small amounts of inhibitors in order to prevent premature reaction, such as, for example: hydroquinone; quinone and tertiary butyl catechol. These monomers, together with the linear polyesters may be admixed together in various proportions as is known in the art in order to obtain resins with varying properties, in amounts of about 1 to 60% by weight; typically, for example, 5 to 45%. Such liquid resin compositions may include a wide variety of other additives, such as, viscosity index improvers; rheological agents; flame retardants; thermoplastic polymers; fillers such as hollow glass or plastic microsphere beads; wood flour; silica; diatomaceous earth; pigments; dyes, stabilizers; glass fibers; release agents; extenders; catalysts; alumina surfactants; and other additives (see, for example, compounds in "Unsaturated Polyester", Modern Plastics Encyclopedia, Volume 50, No. 10a, 1973–1974, pp. 66–68, hereby incorporated by reference).

The components of the polyester resins may be varied as is known in the art to impart the desired properties to the cured resin. Typically, flexible resins employ greater amounts of adipates or azeleates, while more rigid resins use phthalates, both with a variety of different glycols.

Although the foregoing invention has been described in some detail by way of illustration and example for purposes of clarity of understanding, it is understood that certain changes and modifications may be practiced within the spirit of the invention as limited only by the scope of the appended claims.

What is claimed is:

1. A peroxydicarbonate having the formula:

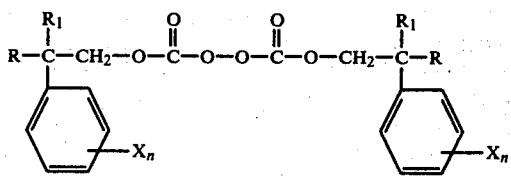

wherein:
each of R and R₁ is lower alkyl of from 1 to 4 carbon atoms;
n is 0 to 3; and
X is selected from the group consisting of lower alkyl of from 1 to 4 carbon atoms, halogen, and lower alkoxy of from 1 to 4 carbon atoms.

2. A composition according to claim 1 wherein R and R₁ are each methyl or ethyl; n is 0 or 1 and X is selected from the group consisting of methyl, ethyl, halogen, methoxy and ethoxy.

3. A composition according to claim 2 wherein X is methyl and n is 1.

4. A composition according to claim 1 wherein n is 0.

5. A composition according to claim 1 wherein R is methyl.

6. A composition according to claim 5 wherein R₁ is methyl.

7. A composition according to claim 5 wherein R₁ is ethyl.

8. Di(2-methyl-2-phenyl propyl) peroxydicarbonate.

9. Di-(2-methyl-2-phenyl butyl) peroxydicarbonate.